US008163554B2

(12) United States Patent
Kandel (10) Patent No.: US 8,163,554 B2
(45) Date of Patent: Apr. 24, 2012

(54) INTERVERTEBRAL DISC

(75) Inventor: Rita Kandel, Toronto (CA)

(73) Assignee: Mount Sinai Hospital, Toronto, Ontario (CA)

(*) Notice: Subject to any disclaimer, the term of this patent is extended or adjusted under 35 U.S.C. 154(b) by 702 days.

(21) Appl. No.: 11/858,716

(22) Filed: Sep. 20, 2007

(65) Prior Publication Data

US 2008/0119936 A1 May 22, 2008

Related U.S. Application Data

(63) Continuation of application No. 10/312,655, filed as application No. PCT/CA01/00972 on Jun. 29, 2001, now abandoned.

(60) Provisional application No. 60/215,002, filed on Jun. 29, 2000.

(51) Int. Cl.
*C12N 5/077* (2010.01)
(52) U.S. Cl. ......... 435/378; 435/402; 435/399; 435/366
(58) Field of Classification Search .................. None
See application file for complete search history.

(56) References Cited

U.S. PATENT DOCUMENTS

| | | | |
|---|---|---|---|
| 5,326,357 | A | 7/1994 | Kandel |
| 5,964,807 | A | 10/1999 | Gan et al. |
| 6,077,989 | A | 6/2000 | Kandel et al. |
| 6,080,579 | A | 6/2000 | Hanley et al. |
| 6,464,729 | B1 | 10/2002 | Kandel |
| 2001/0006948 | A1 | 7/2001 | Kang et al. |
| 2002/0111695 | A1 | 8/2002 | Kandel |
| 2004/0083001 | A1 | 4/2004 | Kandel |
| 2005/0089552 | A1 | 4/2005 | Altman et al. |
| 2005/0260706 | A1 | 11/2005 | Kaplan et al. |
| 2007/0071733 | A1 | 3/2007 | Kandel |
| 2010/0068241 | A1 | 3/2010 | Kandel |
| 2010/0234955 | A1 | 9/2010 | Santerre |

FOREIGN PATENT DOCUMENTS

| | | |
|---|---|---|
| CA | 2285161 | 4/2004 |
| WO | WO 97/17430 | 5/1997 |
| WO | WO 97/45147 | 12/1997 |
| WO | WO 01/29189 | 4/2001 |
| WO | WO2008/098366 | 8/2008 |

OTHER PUBLICATIONS

Okuma et al., "Reinsertion of stimulated nucleus pulposus cells retards intervertebral disc degeneration: An In Vitro and in Vivo experimental study." *Journal of Orthopaedic Research* 18(2000): 988-997.
Mizuno et al., "Tissue engineering of a composite intervertebral disc." *Tissue Engineering* 6:6(2000): 666. XP-002195743.
Gura, "Systems for identifying new drugs are often faulty." *Science* 278(1997): 1041-1042.
Dermer, "Another anniversary for the war on cancer." *Bio/Technology* 12(1994): 320.

Janssen et al., "Morphology and function of rooster efferent ductule epithelial cells in culture." *Tissue & Cell* 30: 5(1998): 554-561.
Aguiar et al., "Notochordal cells interact with nucleus pulposus cells: Regulation of Proteoglycan Synthesis." *Experimental Cell Research* 246(1999): 129-137.
Antoniou et al:, "The Human Lumbar Endplate." *Spine* 23:10(1996): 1153-1161.
Antoniou et al., "The human lumbar intervertebral disc." *J. Clin. Invest.* 98:4(1996): 996-1003.
Aulisa et al., "Immunohistochemical investigation on type III and VI collagen organization in human intervertebral discs in the neonatal period." *Child's Nerv Syst* 14(1998): 104-108.
Bao et al., "The artificial disc: theory, design and materials." *Biomaterials* 17(1996): 1157-1167.
Bayliss et al., "Proteoglycan synthesis in the human intervertebral disc." *Spine* 13:9(1988): 972-981.
Bogduk, "The inter-body joint and the intervertebral discs." *Clinical Anatomy of the lumbar spine and sacrum.* Churchill Livingstone, New York 199713-31.
Borenstein et al., "Epidemiology, etiology, diagnostic evaluation, and treatment of low back pain." *Curr. Opin. in Rheumatology* 11(1999): 151-157.
Boyle et al., "Characterization of proteoglycan accumulation during formation of cartilagenous tissue in vitro." *Osteoarthritis and Cartilage* 3(1995): 117-125.
Buckwalter, "Spine Update. Aging and degeneration of the human intervertebral disc." *Spine* 20:11(1995): 1307-1314.
Chelberg et al., "Identification of hetergeneous cell populations in normal human intervertebral disc." *J. Anat* 186(1995): 43-53.
Chiba et al., "A new culture system to study the metabolism of the intervertebral disc in Vitro." *Spine* 23:17(1998): 1821-1828.
Chiba et al., "Metabolism of the extracellular matrix formed by intervertebral disc cells cultured in alginate." *Spine* 22:24(1997): 2885-1893.
Choy et al., "Percutaneous laser disc decompression." *Journal of Clincial Laser Medecine & Surgery* 16:6(1998): 325-331.
Enker et al., "Artificial disc replacement. Preliminary Report with a 3-year minimum follow up." *Spine* 18:8(1993): 1061-1070.
Evans et al., "Musculoskeletal genetic engineering." *Clincial Orthopaedics and Related Research* 367S(1999): S410-S418.
Eyre, "Biochemistry of the Intervertebral Disc." *International Review of Connective Tissue Research* 8(1979): 227-291.
Gotz et al., "Immunohistochemical localization of the small proteoglycans decorin and biglycan in human intervertebral discs." *Cell Tissue Res* 289(1997): 185-190.
Hadjipavlou et al., "Pathomechanics and clinical relevance of disc degeneration and annular tear: a point-of-view review." *Am. Journ. of Orthopedics* 28(1999): 561-571.
Handa et al., "Effects of hydrostatic pressure on matrix synthesis and matrix metalloproteinase production in the human lumbar intervertebral disc." *Spine* 22:10(1997): 1085-1091.

(Continued)

*Primary Examiner* — Jim Ketter
(74) *Attorney, Agent, or Firm* — Howson & Howson LLP (57) ABSTRACT

The present invention relates to an engineered biological material comprising or enriched for tissue of intervertebral disc; tissue derived from an engineered biological material; constructs comprising one or more tissues from an engineered biological material; methods for producing the engineered biological materials and constructs; and methods of using the engineered biological materials and constructs.

11 Claims, 8 Drawing Sheets

OTHER PUBLICATIONS

Hou et al., "Lumbar intervertebral disc prosthesis. An experimental study." *Chinese Medical Journal* 104:5(1991): 381-386.

Ichimura et al., "Cell culture of the intervertebral disc of rats: Factors influencing culture, proeoglycan, collagen, and deoxyribonucleic acid synthesis." *Journal of Spinal Disorders* 4:4(1991): 428-436.

Inerot et al., "Strucutre and composition of proteoglycans from human annulus fibrosus." *Conn Tiss Res* 26(1991): 47-63.

Inkinen et al., "Relative increase of biglycan and decorin and altered chondroitin sulfate epitopes in the degenerating human intervertebral disc." *J. Rheumatology* 25:3(1998): 506-514.

Ishihara et al., "Effects of hydrostatic pressure on matrix synthesis in different regions of the intervertebrarl disk." *J. Appl. Physiol.* 80(1996): 839-846.

Jahnke et al., "Proteoglycans of the human intervertebral disc." *Biochem. J.* 251(1988): 347-356.

Javedan et al., "Cause of adjacent-segment disease after spinal fusion." *The Lancet* 354:9178(1999): 530-531.

Kawaguchi et al., "Association between an aggrecan gene polymorphism and lumbar disc degeneration." *Spine* 24:23(1999):2456-2460.

Kostuik et al., "Intervertebral disc replacement." *Clinical Orthopaedics and Related Research* 337(1997): 27-41.

Kraemer, "Natural Course and prognosis of intervertebral disc diseases." *Spine* 20:6(1995): 635-639.

Kusior et al., "Tissue engineering of nucleus pulposus in nude mice." *Trans Orthop Society* (1999): 469.

Kupchik et al., "A new method for the three-dimensional in vitro growth of human cancer cells." *Exp Cell Res* 147(1983): 454-460.

Leivseth et al., "Do human lumbar discs reconstitute after chemonucleolysis? A 7-year follow up study." *Spine* 24:4(1999): 342-348.

Maldonado et al., "Inital characterization of the metabolism of intervertebral disc cells encapsulated in microspheres." *J. Orthop. Res.* 10(1992): 677-690.

Melrose et al., "Proteoglycan heterogeneity in the normal adult ovine intervertebral disc." *Matrix Biology* 14(1994): 61-75.

Miller et al., "Lumbar disc degeneration: Correlation with age, sex, and spine level in 600 autopsy specimens." *Spine* 13:2(1988): 173-178.

Nerlich et al., "Immunolocalization of major interstitial collagen types in human lumbar intervertebral discs of various ages." *Virchows Arch* 432(1998): 67-76.

Nishida et al., "Adenovirus-Mediated gene transfer to nucleus pulposus cells: Implication for the treatment of intervertebral disc degeneration." *Spine* 23:22(1998): 2437-2442.

Nishida et al., "Modulation of the biologic activity of the rabbit intervertebral disc by gene therapy: An in vivo study of adenovirus-mediated transfer of the human transforming growth factor β1 encoding gene." *Spine* 24:23(1999): 2419-2425.

Oegema et al., "Aggregated proteoglycan synthesis in organ cultures of human nucleus pulposus." *J. Biol. Chem.* 254:21(1979): 10579-10581.

Oegema et al., "Biochemistry of the intervertebral disc." *Clin Sports Med.* 12:3(1993): 419-439.

Osada et al., "Autocrine-Paracrine mechanism of insulin-like factor-1 secretion, and the effect of insulin-loke growth factor-1 on proteoglycan synthesis in bovine intervertebral discs." *J. Orthop. Res.* 14(1996): 690-699.

Ozaki et al., "Neovasularization of the outermost area of herniated lumbar intervertebral discs." *J. Orthop Sci* 4(1999): 286-292.

Roberts et al., "Proteoglycan components of the intervertebral disc and cartilage endplate: an immunolocalization study of animal and human tissues." *Histochemical Journal* 26(1994): 402-411.

Rufai et al., "The development of fibrocartilage in the rat intervertebral disc." *Anat Embryol* 192(1995): 53-62.

Sato et al., "Phenotypic stability and loss of heterogeneity of rabbit intervertebral disc cells in three-dimensional culture." *Trans Orthop Res Soc* 24(1999): 1026.

Simon et al., "Orthopedic Basic Science." *Am Academy of Orthopedic Surgeons, USA* (1994): 558-568.

Sztrolovics et al., "Age-related changes in fibromodulin and lumican in human intervertebral discs." *Spine* 24:17(1999): 1765-1771.

Sztrolovics et al., "Aggrecan degradation in human intervertebral disc and articular cartilage." *Biochem. J.* 326(1997): 235-241.

Thompson et al., "Stimulation of mature canine intervertebral disc by growth factors." *Spine* 16(1991): 253-260.

Trout et al., "Ultrastructure of the Human Intervertebral disc: II. Cells of the nucleus pulposus." *The Anatomical Record* 204(1982): 307-314.

Urban et al., "Swelling of the intervertebral disc in vitro." *Connect Tissue Res* 9:1(1981): 1-10.

Zeegers et al., "Artificial disc replacement with the modular type SB Charité III: 2-year results in 50 prospectively studied patients." *Eur Spine J.* 8(1999): 210-217.

Reinecke et al., "In vitro transfer von Genen in spinale Gewebe." *Z. Orthop.* 135(1997): 412-416.

Parent U.S. Appl. No. 10/312,655 Office Action dated Apr. 20, 2007.
Parent U.S. Appl. No. 10/312,655 Office Action dated Jul. 31, 2006.
Applicants' Response to U.S. Appl. No. 10/312,655 Office Action dated Jul. 31, 2006.
PCT Search Report for corresponding PCT/CA01/00972, dated Aug. 8, 2002.
PCT IPRP for PCT/CA01/00972, dated Aug. 8, 2002.
Corresponding Canadian Appln No. 2413353 Office Action, dated Aug. 15, 2009.
Corresponding EP Appln No. 01949164.6 Office Action, dated Nov. 4, 2005.
Applicants' Response to EP Appln No. 01949164.6 Office Action, dated Nov. 4, 2005.
Corresponding EP Appln No. 01949164.6 Office Action, dated Oct. 10, 2007.
Applicants' Response to EP Appln No. 01949164.6 Office Action, dated Oct. 10, 2007.
Applicants' Response to Corresponding Canadian Appln No. 2413353 Office Action, dated Aug. 14, 2009.
Corresponding EP Appln No. 01949164.6 Office Communication, dated Nov. 9, 2009.

INTERVERTEBRAL DISC

This application is a Continuation of application Ser. No. 10/312,655, filed on 4 Aug. 2003, and which application(s) are incorporated herein by reference.

FIELD OF THE INVENTION

The present invention relates to an engineered biological material comprising tissue of intervertebral disc: constructs comprising one or more engineered biological materials: methods for producing the biological materials and constructs; and methods of using the biological materials or constructs.

BACKGROUND OF THE INVENTION

The human spine consists of thirty-three vertebral bodies of which the distal nine are fused to form the sacrum and coccyx (Simon, S R, et al 1994; Bogduk, N., 1997). The 24 vertebrae, with the exception of C1 and C2, are each separated by an intervertebral disc (IVD). The IVD anchors adjacent vertebral bodies and by doing so allows for spinal stabilization, load bearing, and movement. The intervertebral disc is a specialized structure consisting of two interdependent tissues, the annulus fibrosus (AF) and the nucleus pulposus (NP) which merge with the cartilage endplate (Bogduk, N., 1997; Eyre, D R, 1979). The composition of the AF and nucleus pulposus varies with anatomical site in the tissue and the age of the individual (Eyre, D R, 1979; Buckwalter, 1995). The normal function of the disc is dependent on maintenance of the composition, organization, and integrity of the different components (Chiba, 1998). The annulus fibrosus is responsible for withstanding circumferential tensile forces, while the nucleus pulposus resists compressive forces during normal activity (Simon, 1994; Bogduk, 1997; Eyre, 1979; Buckwalter, 1995). The disc is relatively avascular as only the outer portion of the annulus contains blood vessels in adults (Buckwalter, 1995). The disc cells rely on diffusion of nutrients from these vessels and from blood vessels in the vertebral body.

The annulus fibrosus surrounds the nucleus pulposus and consists of approximately 10-20 lamellar sheets each composed of collagen fibres oriented parallel to each other and about 65° from the vertical. Although the angle is the same, the direction of the inclination alternates with each sheet such that the fibres in one lamella are 65° to the right, while in the next lamella they are 65° to the left. Every second lamella has the same orientation (Bogduk, N., 1997). This very specific collagen organization allows the disc to rotate and flex. Collagen makes up about 70% of the dry weight of the annulus (Buckwalter, 1995). Type I collagen is the predominate collagen, but types II, III, V, VI and type IX collagen are also present in lesser amounts (Bogduk, N., 1997; Buckwalter, 1995; Nerlich, 1998). The average diameter of the collagen fibril is 50-60 nm as determined by transmission electron microscopy (Eyre, 1979). The annulus also contains a small amount of proteoglycans and these also have a specific distribution. The proteoglycan content in the tissue is lowest in the periphery of the annulus fibrosus and increases in amount towards the nucleus pulposus (Bogduk, N., 1997). The major proteoglycan is aggrecan (Bogduk, N., 1997; Inerot, 1991; Roberts, 1994; Antoniou, 1996; and Sztrolovics, 1997). Small proteoglycans such as decorin, biglycan, and fibromodulin are also present (Gotz, 1997; Sztrolovics, 1999). Elastin and other non-collagenous proteins are detected in the disc (Bogduk, 1997). The cellularity across the annulus varies, as it is more cellular in the outer third (0.7 µg DNA/gm dry weight) when compared to the inner two-thirds (0.1 µg DNA/gm dry weight) of the annulus (Bayliss, 1998).

The nucleus pulposus (NP) is gelatinous type tissue, which is surrounded by the annulus fibrosus and confined by the cartilagenous endplates of the vertebral bodies (Bogduk, 1997). It consists of proteoglycans within a loose network of collagen and does not show the same degree of collagen organization in the matrix as the annulus fibrosus (Eyre, 1979; Aguiar, 1999). Proteoglycans comprise approximately up to 65% of the dry weight of the nucleus. Aggrecan is the major proteoglycan present in the nucleus pulposus and about 60% of it is present in a form that does not aggregate. Other proteoglycans, such as decorin, biglycan, and fibromodulin, are also present (Buckwalter, 1995; Gotz, 1997; Sztrolovics, 1999; and Oegema, 1993). The nucleus pulposus contains predominately type II collagen but there are other collagen types present, such as III, VI, IX, and XI (Eyre, 1979; Buckwalter, 1995; Aulisa, 1998). Type I collagen has been detected in small amounts in the nucleus pulposus of humans (Eyre, 1979) and rats (Rufai, 1995). The average diameter of the collagen fibrils is around 30 nm as determined by transmission electron microscopy (Eyre, 1979). In childhood, the nucleus contains notochordal cells but these disappear with age. It has been postulated that these cells contribute to the maintenance of the nucleus pulposus and their absence in the adult disc explains the high prevalence of disc degeneration (Aguiar, 1999).

The other component of the disc is the cartilage endplate, a thin layer of articular cartilage that is integrated with the underlying bone of the vertebral body (Bogduk, 1997). As the endplate covers a portion of the vertebral body it confines the nucleus pulposus entirely but only a portion of the annulus fibrosus. The peripheral portion of the annulus fibrosus inserts directly into the bone. The endplate is considered part of the disc as it can easily be separated from the vertebral body (Bogduk, 1997). Like articular cartilage, the endplate consists predominately of water, proteoglycans and collagen (Bogduk, 1997; Antoniou, 1996). The zone of tissue closer to the bone is richer in collagen as compared to the zone closer to the nucleus pulposus, which contains less collagen and more proteoglycans and water (Bogduk, 1997).

Intervertebral disc prolapse is a very common problem and currently there is no optimal treatment for persistent disease. In an autopsy study, 97% of individuals 50 years or older showed disc degeneration (Miller, 1988). It is not known why it is so common, but may be due in part to the relative avascularity of the tissue until there is prolapse (Ozaki, 1999), mechanical factors (Hadjipavlou, 1999), the absence of notochordal cells (Aguiar, 1999) or genetic factors (Kawaguchi, 1999). The back pain that can develop as a result of this disease is often self-limited, but a percentage of affected individuals require surgery (Kraemer, 1994; Borenstein, 1999). Although the surgical intervention may relieve pain faster, this procedure does not restore disc height or its original load bearing capacity. Post-discotomy syndrome, which is characterized by persistent pain and occurs after disc surgery, may be treated by spinal fusion. This is a less than optimal treatment as it is not always successful and results in limited flexibility and degenerative changes in adjacent vertebrae (Javedan, 1999).

IVD replacement, with allografts or prosthetic devices, has been attempted but met with limited success (Leivseth, 1999; Hou, 1991; Enker 1993; Bao, 1996; and Kostiuk, 1997). Alternative treatments such as laser treatment are now being studied (Zeegers, 1999). Intraspinal injection of chymopapain has been used; however, a recent study of 51 patients showed that this treatment had no effect (Choy, 1998). Although not used currently, gene therapy may be another way to treat this disease (Nishida, 1998; Nishida, 1999; and Evans & Robbins, 1999). There is clearly a need to develop novel approaches to the treatment of disc disease.

SUMMARY OF THE INVENTION

The present inventor has produced an engineered biological material comprising or enriched for one or more tissues of intervertebral disc.

In particular, the present inventor has produced an engineered biological material comprising a continuous layer of nucleus pulposus tissue. The tissue formed in vitro was characterized and compared to in vivo nucleus pulposus tissue and it was found to mimic the organization of nucleus pulposus tissue in vivo. In particular, the accumulation of sulfated proteoglycans in the nucleus pulposus tissue continued up to 10 weeks and this was paralleled by an increase in tissue thickness and dry weight. DNA content decreased over time. The amount of DNA and proteoglycans per mg dry weight of the tissue generated in 10 weeks old cultures were substantially the same as for the in vivo tissue. There was no significant difference between in vitro and in vivo tissues. The cells in culture synthesized large proteoglycans which were similar in size to those synthesized by cells in nucleus pulposus tissue explant culture as determined by Sepharose CL-2B column chromatography. The cells also synthesized type II collagen.

Therefore, in one aspect, the invention relates to an engineered biological material comprising a continuous layer of nucleus pulposus tissue. In an embodiment, an engineered biological material is provided comprising in combination a substrate and a continuous layer of nucleus pulposus tissue on the substrate.

In an embodiment, the invention provides an engineered biological material comprising in combination nucleus pulposus tissue and a substrate for the nucleus pulposus tissue, the nucleus pulposus tissue being reconstituted on the substrate in vitro from isolated nucleus pulposus cells and being a continuous layer comprising nucleus pulposus cells and an extracellular matrix containing sulfated proteoglycans and type II collagen.

In another aspect, the invention relates to an engineered biological material comprising a continuous layer of annulus fibrosus tissue. In an embodiment the biological material comprises in combination a substrate and a continuous layer of annulus fibrosus tissue on the substrate.

In an embodiment, the invention provides an engineered biological material comprising in combination annulus fibrosus tissue and a substrate for the annulus fibrosus tissue, the annulus fibrosus tissue being reconstituted on the substrate in vitro from isolated annulus fibrosus cells and being a continuous layer comprising annulus fibrosus cells and an extracellular matrix.

In another aspect of the invention an engineered biological material is provided comprising a continuous layer of nucleus pulposus tissue surrounded by annulus fibrosus tissue.

The invention also relates to nucleus pulposus tissue and/or annulus fibrosus tissue derived from the engineered biological materials of the invention.

Still further the invention contemplates an intervertebral disc construct comprising nucleus pulposus or annulus fibrosus tissue derived from a biological material of the invention fused to a substrate (e.g. bone substitute). A construct is also provided comprising nucleus pulposus tissue derived from a biological material of the invention fused to a continuous layer of cartilage tissue on a substrate. The nucleus pulposus tissue may be surrounded by a continuous layer of annulus fibrosus tissue.

The invention also relates to a process for producing an engineered biological material of the invention comprising isolating nucleus pulposus cells or annulus fibrosus cells from intervertebral disc; forming a layer of the nucleus pulposus cells or annulus fibrosus cells on a substrate, and; culturing the nucleus pulposus cells or annulus fibrosus cells in growth media under suitable conditions so that the nucleus pulposus cells or annulus fibrosus cells accumulate extracellular matrix and form nucleus pulposus tissue or annulus fibrosus tissue, respectively.

The invention also provides a process for producing an engineered biological material of the invention comprising isolating nucleus pulposus cells and annulus fibrosus cells from intervertebral disc; forming a layer of the nucleus pulposus cells surrounded by the annulus fibrosus cells on a substrate, and; culturing the nucleus pulposus cells and annulus fibrosus cells in growth media under suitable conditions so that the nucleus pulposus cells and annulus fibrosus cells accumulate extracellular matrix and form nucleus pulposus tissue surrounded by annulus fibrosus tissue.

In an embodiment the substrate is selected from the group consisting of bone, an engineered biomaterial preferably an engineered bone substitute, and porous tissue culture inserts.

The nucleus pulposus cells or annulus fibrosus cells in the engineered biological materials or constructs of the invention may be transformed with recombinant vectors containing an exogenous gene encoding a biologically active protein that corrects or compensates for a genetic deficiency, or stimulates cell growth or stimulates extracellular matrix production by cells, or alternatively, encoding a drug. Therefore, the invention also contemplates an engineered biological material or construct of the invention wherein nucleus pulposus cells or annulus fibrosus cells in the biological material or construct are transformed with recombinant vectors containing an exogenous gene encoding a biologically active protein which can correct or compensate for a genetic deficiency or have a stimulatory effect, or encoding a drug.

The invention still further relates to a system for testing a substance or agent that affects nucleus pulposus tissue or annulus fibrosus tissue comprising: generating or culturing a biological material, or construct of the invention in the presence of a substance or agent which is suspected of affecting nucleus pulposus tissue or annulus fibrosus tissue, and determining the biochemical composition and/or physiological organization of tissue generated or cultured, with the biochemical composition and/or physiological organization of the biological material or construct generated or cultured in the absence of the substance or agent.

The invention still further relates to a method of using the biological materials and constructs of the invention to test pharmaceutical preparations for efficacy in the treatment of diseases of intervertebral disc.

Still another aspect of the present invention provides a method of conducting a drug discovery business comprising:
  (a) identifying agents that affect the biochemical composition and/or physiological organization of an engineered biological material of the invention;
  (b) conducting therapeutic profiling of agents identified in step (a), or further analogs thereof, for efficacy and toxicity in animals; and
  (c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

Yet another aspect of the invention provides a method of conducting a target discovery business comprising:

(a) providing one or more engineered biological materials for identifying agents by their ability to affect the biochemical composition and/or physiological organization of the engineered biological material;

(b) (optionally) conducting therapeutic profiling of agents identified in step (a) for efficacy and toxicity in animals; and (c) licensing, to a third party, the rights for further drug development and/or sales for agents identified in step (a), or analogs thereof.

The invention provides methods of using an engineered biological material or tissues obtained therefrom or construct of the present invention as an implant to replace or repair damaged or deficient intervertebral disc, and methods for repairing damaged or degenerated intervertebral discs. Methods of the invention may be used to treat vertebrates suffering from degenerated intervertebral disc conditions, and in particular to treat humans with such conditions.

Therefore, the invention contemplates a method of replacing or repairing damaged or deficient intervertebral discs or portions thereof (preferably nucleus pulposus) of a patient comprising implanting an engineered biological material (or tissue therefrom) or construct of the invention into the site of the damaged or deficient intervertebral disc of the patient. Methods for enhancing healing of an intervertebral disc in a patient are contemplated which comprise inserting a biological material (or tissue therefrom) or construct of the invention into the site of a damaged intervertebral disc.

In an embodiment, the invention provides a method for replacing or repairing a degenerated or damaged nucleus pulposus tissue of an intervertebral disc comprising implanting in the disc space, after the removal of the degenerated or damaged nucleus pulposus tissue, an engineered biological material of the invention comprising a continuous layer of nucleus pulposus tissue or nucleus pulposus tissue obtained therefrom.

In an embodiment, the invention provides a method for replacing or repairing a degenerated or damaged annulus fibrosus tissue of an intervertebral disc comprising implanting in the disc space, after the removal of the degenerated or damaged annulus fibrosus tissue, an engineered biological material of the invention comprising a continuous layer of annulus fibrosus tissue or annulus fibrosus tissue obtained therefrom.

In an aspect of the invention, a method for repairing damaged or degenerated intervertebral discs is provided comprising evacuating tissue from the nucleus pulposus portion of a degenerated intervertebral disc space, preparing a biological material of the invention using nucleus pulposus cells from the evacuated tissue, and implanting the biological material in the evacuated nucleus pulposus space.

In another aspect of the invention, a method for repairing damaged or degenerated intervertebral discs is provided comprising evacuating tissue from the annulus fibrosus portion of a degenerated intervertebral disc space, preparing a biological material of the invention using annulus fibrosus cells from the evacuated tissue, and implanting the biological material in the evacuated annulus fibrosus space.

The invention also contemplates methods for using the biological materials and constructs of the invention in gene therapy.

A biological material or construct of the invention can be used as an in vitro model for investigating the metabolism and degeneration of nucleus pulposus or annulus fibrosus cells and tissues.

These and other aspects of the present invention will become evident upon reference to the following detailed description and attached drawings.

DESCRIPTION OF THE DRAWINGS

The invention will be better understood with reference to the drawings in which.

DETAILED DESCRIPTION OF PREFERRED EMBODIMENTS OF THE INVENTION

The present invention relates to an engineered biological material comprising a continuous layer of nucleus pulposus tissue. The tissue is characterized by nucleus pulposus cells that synthesize large sulfated proteoglycans and type II collagen characteristic of nucleus pulposus cells in vivo. The tissue in the biological material is also characterized by becoming less cellular with age. The nucleus pulposus tissue is further characterized by having a three dimensional organization that is characteristic of nucleus pulposus tissue in vivo.

In an embodiment, the engineered biological material comprises a continuous layer of nucleus pulposus tissue with a thickness of between about 100 to 500 µm after histological processing.

The present invention also relates to an engineered biological material comprising a substrate and a continuous layer of nucleus pulposus tissue on the substrate.

The invention also relates to an engineered biological material comprising a substrate and a continuous layer of annulus fibrosus tissue on the substrate. The annulus fibrosus cells are characterized by being capable of synthesizing types I and II collagen and proteoglycans similar in size to those synthesized by annulus fibrosus cells in vivo. The annulus fibrosus tissue is further characterized by having a three dimensional organization that is characteristic of annulus fibrosus tissue in vivo.

The invention also relates to a method for producing an engineered biological material of the invention comprising isolating nucleus pulposus cells or annulus fibrosus cells of intervertebral disc; forming a layer of the cells on a substrate; culturing the cells in growth media under suitable conditions so that the cells accumulate intracellular matrix and form a continuous layer of nucleus pulposus or annulus fibrosus tissue.

The cells used in the method of the invention may be isolated from intervertebral discs (lumbar discs, thoracic discs, or cervical discs) from animals, preferably humans, bovines, ovines, rabbits, most preferably humans. The tissue may be isolated from adult or fetal tissue. In one embodiment of the invention, the cells are isolated from intervertebral disc of the lumbar spine of sheep. Intervertebral disc tissue may be extracted from a patient being treated, or alternatively from a donor, using known surgical techniques.

The nucleus pulposus or annulus fibrosus cells may be isolated from intervertebral disc tissue by sequential enzyme digestion techniques, such as those described in Boyle et al, Osteoarthritis and Cartilage 3, 117-125, 1995. For example, the cells may be treated with 0.5% protease followed by 0.1% bacterial collagenase.

In accordance with the method of the invention a continuous layer of cells is placed on a substrate. Suitable substrates include bone, engineered biomaterials, and porous tissue culture inserts, for example filter inserts.

The substrate is optionally coated with an attachment factor. Attachment factors are known in the art, see for example, Streuli and Bissell, J. Cell. Biol. 110:1405, 1990 and Buck and Horwitz, Ann, Rev. Cell Biol. 3:179, 1987. Examples of attachment factors include type I collagen, type II collagen, type IV collagen, a synthetic peptide of a segment of collagen, (e.g. a fifteen amino acid sequence 766GTPGPQ-GIAGQRGVV780 which is present in the α1 chain of collagen) (Bhatnagar and Qian, 38th Annual Meeting of the Orthopedic Research Society 17:106, 1992), fibronectin, gelatin, laminin, polylysine, vitronectin, cytotactin, echinonectin, entactin, tenascin, thrombospondin, uvomorulin, biglycan, chondroitin sulfate, decorin, dermatan sulfate, and heparin. A preferred attachment factor that may be used in the method of the invention is collagen, most preferably type II collagen. When the substrate is coated it may be air dried and sterilized.

In a preferred embodiment of the invention the substrate is a tissue culture insert known as Millicell CM®, (Millipore Corp., Bedford, Mass., U.S.A.), pore size 0.4 µm, coated with an attachment factor, preferably type II collagen (Sigma Chemical Co., St. Louis, Mo., U.S.A.).

The substrate may be a bone substitute, in particular an engineered bone substitute such as coral derivatives (Interpore International Inc., CA), deproteinized bovine bone (Bio-oss®, Geistlich Biomaterials, Switzerland), or a porous biodegradable biomaterial which is formed from sintered calcium polyphosphate (CPP) as described in U.S. Pat. No. 6,077,989 to Kandel et al. and PCT Application No. PCT/CA97/00331 (WO97/45147 published Dec. 4, 1997). A sintered porous CPP can be formed with a preferred pore size and percent porosity through selection of sintering parameters (time, temperature, starting particle size). Thus, structures can be formed that more closely mimic the structure of the bone into which a composite construct of the invention may be placed. Additionally, degradation rates can be controlled to some extent through control of percent porosity and pore size (i.e. total free surface area). In an embodiment, the substrate is an appropriately-sized porous disc (e.g. 4 mm diameter and 3 mm thick) that may be encased with an inert tubing to help cell retention by preventing overflow.

Cartilage can be formed on, and anchored to, an engineered bone substitute, preferably a porous CPP substrate. Articular chondrocytes may be cultured on a porous CPP disc to form a continuous layer of cartilagenous tissue using the method described in U.S. Pat. No. 5,326,357.

Nucleus pulposus or annulus fibrosus cells may be seeded on a selected substrate at a cell density of about to $1 \times 10^5$ to $8 \times 10^6$ cells/cm$^2$, preferably $2$-$4 \times 10^6$ cells/cm$^2$, more preferably $3$-$3.5 \times 10^6$ cells/cm$^2$, most preferably $3.3 \times 10^6$ cells/cm$^2$. The cells seeded on a coated or uncoated substrate are grown in suitable culture conditions. Examples of suitable culture media are known in the art, such as Ham's F12 and/or Dulbecco's modified Eagle's medium (DMEM). Preferably DMEM is used. The culture medium may contain serum, for example, heat inactivated fetal bovine serum in a concentration range of about 2-20%, preferably 10-20%, and may further contain growth factors, and optionally ascorbic acid. The culture media is applied above and below the substrate. The cells may be cultured at 37° C. in a humidified atmosphere supplemented with $CO_2$.

In a preferred embodiment of the invention, the isolated cells are grown in DMEM containing 10% fetal bovine serum for about 5 days, the medium is then changed to DMEM containing 20% fetal bovine serum, and ascorbic acid (100 µg/ml, final concentration) at about 7 days.

The cells are cultured for an additional 5 weeks to obtain the engineered biological material described herein. The cells may be cultured for less than 5 weeks, or greater than 5 weeks, to obtain a product which may be suitable for some uses such as transplantation or gene therapy.

Mechanical force(s) may be administered during in vitro formation of the engineered biological material in order to enhance the development of tissues that are highly suited for implantation and physiological weight bearing. Torsion, compression, and/or shear forces may be applied during tissue formation. Forces, together or alone, may be applied, consecutively, simultaneously, or cyclically. The mechanical forces may be applied through the use of a mechanical stimulation system that allows for loading cell cultures under sterile conditions. For example, the Mach-1™ system (Biosyntech, Montreal) is capable of supplying simultaneous compressive and linear shear forces, and can include the application of torsional shear forces. For each type of force application, a skilled artisan can determine the optimal conditions to induce tissue growth and organization (i.e. force amplitude, frequency and duration of stimulation).

In an embodiment of the invention, either sinusoidal compressive or torsional forces are applied to the developing tissue. Compressive forces may be applied at about day 3, in a range of unconstrained loading between 0.1 to 10 N (approximately corresponding to compressive stresses of 0.01 to 1 MPa), through a compliant, biocompatible, autoclavable elastomer (e.g. medical grade silicone or polyurethane) placed on the actuator to avoid direct contact with the cells. The duration of loading may range from 100 to 1200 cycles/day and may be applied at a frequency of 1.0 Hz. (1 Hz approximates normal gait frequency of disc loading). Minimal numbers of loading cycles may be preferred to stimulate organization of IVD tissues. For example, 20 sec. of 1 MPa of hydrostatic pressure may be sufficient to stimulate proteoglycan synthesis by inner annulus cells.

Torsional shear force application may consist of a compressive preload followed by varying degrees of cyclic torsional shear. Angular deformation amplitudes ranging from 0.005 rad to 0.05 rad at a frequency of 1 rad/sec, may be used (approximately corresponding to a maximal torque of 0.5N·mm). Cyclic compressive and torsional shear forces may be simultaneously applied.

The invention also contemplates an intervertebral disc construct. The construct may comprise one or both of annulus fibrosus and nucleus pulposus tissue, with cartilagenous tissue and/or a substrate (e.g. bone substitute). In one embodiment, the construct comprises an engineered bone substitute with cartilagenous tissue formed thereon, and nucleus pulposus tissue derived from an engineered biological material of the invention fused to the bone substitute-cartilagenous tissue. This construct may be prepared by culturing articular chondrocytes on porous CPP discs for about 3 weeks using the methods described in U.S. Pat. No. 5,326,357. Simultaneously, nucleus pulposus cells may be grown on a substrate, preferably a filter insert, more preferably a Millipore CM® filter as described herein. At about 3 weeks, a piece of nucleus pulposus tissue formed in vitro may be punched out from the substrate (e.g. Millipore CM® filter), and placed on the CPP-cartilagenous tissue construct. The tissue components may be held together using fibrin glue, or other suitable adhesive, and maintained in culture for about 3 weeks. The composite may be harvested to form the construct.

In another embodiment of the invention, the construct resembles a natural disc. Thus, a substrate (e.g. bone substitute) may be made with a central depression, and articular cartilage tissue may be cultured in the depression. Articular cartilage tissue may be cultured in the depression using the methods described in U.S. Pat. No. 5,326,357. Annulus fibrosus tissue derived from an engineered biological material of the invention (or other source) may be grown on the cartilagenous tissue formed on the substrate. After fusion of the annulus fibrosus and cartilagenous tissues, a plug of annulus fibrosus tissue may be removed from the centre of the annulus fibrosus tissue and replaced with nucleus pulposus tissue derived from an engineered biomaterial of the invention. The resulting composite comprising annulus fibrosus, nucleus pulposus, cartilage endplate, and substrate is grown in culture to produce a construct comprising fused annulus fibrosus tissue, nucleus pulposus tissue, and cartilage tissue, with a substrate.

In a specific embodiment of the invention a calcium polyphosphate porous cylinder may be generated that has a central depression on its surface. Articular chondrocytes may be isolated (e.g. from sheep knee joint) (Boyle et al, Osteoarthritis and Cartilage 3, 117-125, 1995) and plated in the depression. The cells may be grown under the tissue culture conditions described in U.S. Pat. No. 5,326,357 for about 3 weeks during which time they will form cartilagenous tissue. Annulus fibrosus and nucleus pulposus cells may be isolated from sheep lumbar spine. The nucleus pulposus cells may be plated on a substrate, preferably filter inserts (e.g. Millicell CM®, Millipore Corp) and grown as described herein for about 4 weeks. At about 4 weeks, the nucleus pulposus tissue formed in vitro has sufficient strength to be handled. The annulus fibrosus cells are plated on top of the cartilagenous tissue which has formed on the CPP porous cylinder. This composite may be grown in culture for about 4 weeks under the optimal loading conditions as described herein. At about 4 weeks, a plug of annulus fibrosus tissue (e.g. 1-3 mm, preferably 2 mm diameter) is punched out from the centre and a plug of nucleus pulposus tissue (obtained from the nucleus pulposus tissue culture) is placed in the resulting defect. This composite consisting of annulus fibrosus, nucleus pulposus, cartilage endplate and CPP may be grown in culture for an additional 4 to 6 weeks as described herein.

In an embodiment, nucleus pulposus cells are plated in the center of a substrate (e.g. disc) with annulus cells surrounding them, and grown in culture together in the presence or absence of mechanical stimulation.

The engineered biological material and constructs of the present invention can be used as model systems for in vitro studies of intervertebral disc (or components thereof i.e. annulus fibrosus and nucleus pulposus tissue) function and development.

In accordance with one embodiment of the invention, an engineered biological material, may be used to test substances which affect intervertebral disc or components thereof (e.g. nucleus pulposus or annulus fibrosus tissue). A system for testing a substance that affects intervertebral disc in accordance with the invention comprises generating or culturing an engineered biological material or construct of the invention in the presence of a substance which is suspected of affecting intervertebral disc or components thereof, and determining the biochemical composition and/or physiological organization of tissue generated or cultured, and comparing with the biochemical composition and/or physiological organization of the engineered biological material in the absence of the substance.

The substance may be added to the culture or the cells in the engineered biological materials (nucleus pulposus or annulus fibrosus cells) may be genetically engineered to express the substance i.e. the cells may serve as an endogenous source of the substance. Cells may be engineered by viral or retroviral-mediated gene transfer using methods known in the art to produce a specific substance. The engineered cells are constructed and maintained such that they release the substance into the medium for the desired period of time for the culture.

The system may be used to analyze the effects of substance(s) on different stages of intervertebral disc development. Effects on cells at very early, intermediate, and late stages of development may be evaluated by assessing the biochemical composition and/or physiological organization of the tissue generated in the cultures at various times such as 2, 4, 6 and 8 weeks.

The biochemical composition and/or physiological organization of the tissue generated in the cultures may be assessed using the methods described herein. (See, for example, the methods described in Example 1)

In a preferred embodiment of the invention, the biological materials of the present invention may be used in the testing of pharmaceutical preparations useful in the treatment of diseases of intervertebral disc.

The biological materials of the invention may also be implanted into patients to replace or repair damaged or deficient intervertebral disc. In particular, the biological materials of the invention may be implanted into individuals with idiopathic scoliosis, herniated disc, degenerative disc disease, recurrent disc herniation, or spinal stenosis.

It is also contemplated that the biological materials of the present invention can be used to enhance healing of damaged or deficient intervertebral discs when inserted into the site of the disc.

The invention also contemplates using the biological materials of the invention in gene therapy. Therefore, recombinant vectors containing an exogenous gene encoding a biologically active protein that is selected to modify the genotype and/or phenotype of a cell to be infected may be introduced into cells in the biological materials of the invention. An exogenous gene coding for a biologically active protein which corrects or compensates for a genetic deficiency or a drug may be introduced into cells in the biological materials. For example, IGF-I could be introduced into the cells so that the cells secrete this protein and stimulate production of proteoglycans resulting in disc regeneration. The expression of the exogenous gene may be quantitated by measuring the expression levels of a selectable marker encoded by a selection gene contained in the recombinant vector.

The following non-limiting examples are illustrative of the present invention:

EXAMPLE 1

The following materials and methods were utilized in the investigations outlined in the examples:
Materials and Methods
Cell Cultures The lumber spines from up to 9 month-old sheep were removed. The muscle tissue was cleared from the ventral portion of the spine and then the ligamentous tissue surrounding the disc was carefully excised aseptically and discarded. The annulus fibrosus (AF) and nucleus pulposus (NP) were identified and the nucleus pulposus was dissected out with blunt forceps and placed in Ham's F12. The accuracy of the dissection was determined by submitting random tissue fragments for paraffin embedding and histological assessment at each harvesting.

The tissue underwent sequential enzyme digestion consisting of 0.5% protease (Sigma Chemical Co., St. Louis, Mo., USA) for 1 hr at 37° C., followed by 0.1% collagenase (Boehringer Mannheim GmbH, Indianapolis Ind., USA) overnight at 37° C. The cell suspension was then filtered through a sterile mesh and plated at a cell density of $3.3 \times 10^6/cm^2$ on filter inserts (Millicell CMR® Millipore Corp., Bedford, Mass.) precoated with type II collagen (Sigma Chemical Co., St. Louis, Mo., USA) as described previously (Kandel 1997, Yu 1997). The cells were grown in Dulbecco's Modified Eagles medium (DMEM) supplemented with 10% fetal bovine serum (FBS). After 5 days the FBS was increased to 20% and ascorbic acid (100 µg/ml, final concentration) was added to the medium at day 7. The medium was changed every 2-3 days and fresh ascorbic acid was added each time. The cultures were harvested at 2, 4, 6, 8, and 10 weeks for histologic assessment and biochemical analysis.

Histology

The nucleus pulposus cell cultures were harvested at selected intervals and fixed in 10% formalin. They were paraffin-embedded and 5 µm sections were cut and stained with either hematoxylin and eosin or toluidine blue. Toluidine blue stains sulphated proteoglycans.

The culture tissue thickness was measured morphometrically using light microscopy and a digitized board connected to an IBM computer equipped with the Bioquant Image Analysis program. Ten separate points in each section were examined and three sections per culture were quantified. Tissue thickness was calculated by determining the mean value of three separate experiments.

Determination of Dry Weight of Culture Tissue

The cultures, harvested at various times, and representative fragments of the in vivo nucleus pulposus were lyophilized overnight. The lyophilized tissues were weighed on an electrical balance (Mettler Instruments, AG, Greifensee-Zurich, Switzerland).

DNA Quantification

The cultures at different time points and representative fragments of the in vivo nucleus pulposus tissue were digested with papain [40 ug/ml in buffer consisting of 20 mM ammonium acetate, 1 mM ethylenediaminetetraacetic acid (EDTA) and 2 mM dithiotreitol] for 48 hours at 65° C. The DNA content was measured using Hoescht 33258 dye (Polysciences, Inc., Warrington, Pa.) and fluorometry (emission wavelength 365 nm and excitation wavelength 458 nm) as described by Kim et al. (1988). Calf thymus DNA (Sigma Aldrich Co., St. Louis, Mo., USA) was used to generate the standard curve.

Quantification of Proteoglycans and Collagen

Proteoglycan content in the in vitro formed tissue and the in vivo tissue was determined by measuring the amount of glycosaminoglycans in the papain digest using the dimethylmethylene blue dye binding assay (Polysciences Inc., Warrington, Pa.) and spectrophotometry as described by Farndale et al. (1986) and modified by Goldberg et al (1990). Chondroitin sulphate (Sigma Aldrich Co., St. Louis, Mo., USA) was used to generate the standard curve.

The collagen content was determined by measuring the amount of hydroxyproline in the papain digests of the cultures. An aliquot was hydrolyzed overnight at 110° using 12N hydrochloric acid. The hydroxyproline was measured by high pressure liquid chromatography using a C18 reverse column and a Waters PicoTag amino acid analysis system. The amount of collagen was calculated from the hydroxyproline content which comprises about 10% of the weight of collagen (Berg, R A, 1982, Determination of 3 and 4 hydroxyproline. In Methods of Enzymology pp. 393-94, Ed. by L. W. Cunningham and D. W. Frederiksen, New York, Academic Press, 1982).

Analysis of Newly Synthesized Proteoglycans

To analyze proteoglycan biosynthesis, 8 week old cultures were incubated with [$^{35}$S]-sulphate (4 µCi/per well) for 24 hours prior to harvesting. Matrix proteoglycans were extracted with 4M guanidine hydrochloride in 50 mM sodium acetate, pH 5.8 containing protease inhibitors (0.1M 6-amino-hexanoic acid, 50 mM benzamidine HCl, 10 mM EDTA and 5 mM N-ethylmaleimide) for 24 hours at 4° C. The proteoglycans were precipitated by the addition of three volumes of ice cold ethanol. After 24 hours at 4° C. the precipitate was collected, washed with 70% ethanol, and resuspended in 4 M guanidium HCl with protease inhibitors. Proteoglycan synthesis was determined by quantitating [$^{35}$S]-sulphate incorporation by a β-scintillation counter. The proteoglycan size was determined by Sepharose CL-2B column chromatography (1×100 cm) under dissociative conditions, as described previously (Boyle 1995). Fractions (2 ml) were collected using a flow rate of 6 ml/hour at 4° C. The elution profile was analyzed for its partition coefficient [$K_{av}$=(Ve−Vo)/Vt−Vo), where Vo=void volume, Vt=total volume, Ve=elution volume]. Vt was determined using [$^{35}$S]-sulphate and Vo was determined using dextran blue 2000.

Sheep ex vivo nucleus pulposus explant cultures were established as controls. Immediately after being placed in culture the cultures were labelled for 24 hours with [$^{35}$S]-sulphate and proteoglycans were extracted identically as described for the filter cultures.

Analysis of Collagens

The 8 week old cultures were harvested and digested with pepsin (200 μg/ml in 0.1 N acetic acid; Sigma Aldrich Co., St. Louis, Mo., USA) for 72 hours at 4° C. The pepsin extracts were separated on a 5% sodium dodecyl sulfate-polyacrylamide gel (SDS-PAGE) and either silver stained (Silver Stain Plus Kit, Bio-Rad, Hercules, Calif.) or transferred to nitrocellulose membranes (Schleicher & Schuell, Keene, N.H., USA) for Western blot analysis. The presence of type II collagen was determined by Western blot using antibody reactive with type II collagen (4 μg/ml. monoclonal clone 6B3; NeoMarkers, Union City, Calif., USA). Immunoreactive bands were visualized by a chemiluminescence using peroxidase-labelled secondary antibodies (Western blotting kit, Boehringer Mannheim GmbH, Indianapolis, Ind., USA).

Statistical Analysis

Student's t-test was used to analyse the data and significance assigned at a p value<0.05.

Results

Histologic Appearance of Cultures

Figure 1A:
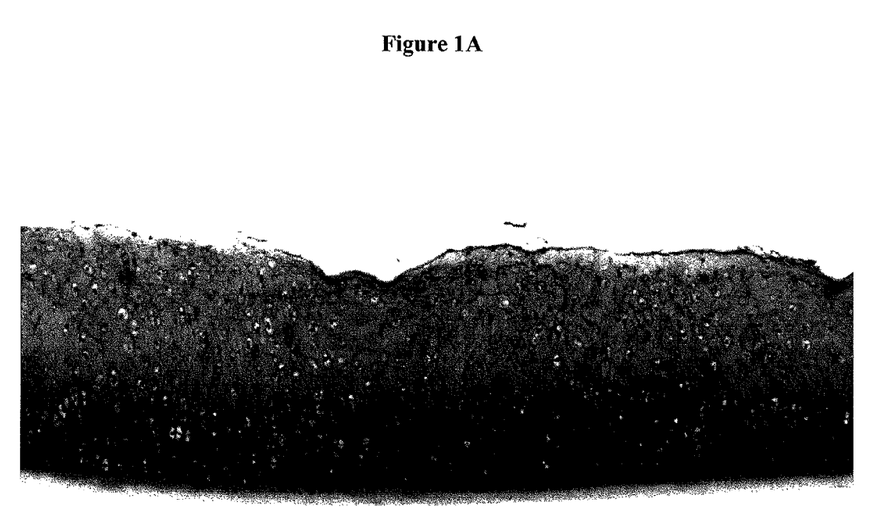
FIG. 1A is a photomicrograph of toluidine blue-stained section of 10 wk old formalin-fixed, paraffin-embedded nucleus pulposus cell cultures showing the formation of nucleus pulposus tissue. The filter is still present.
Figure 1B:
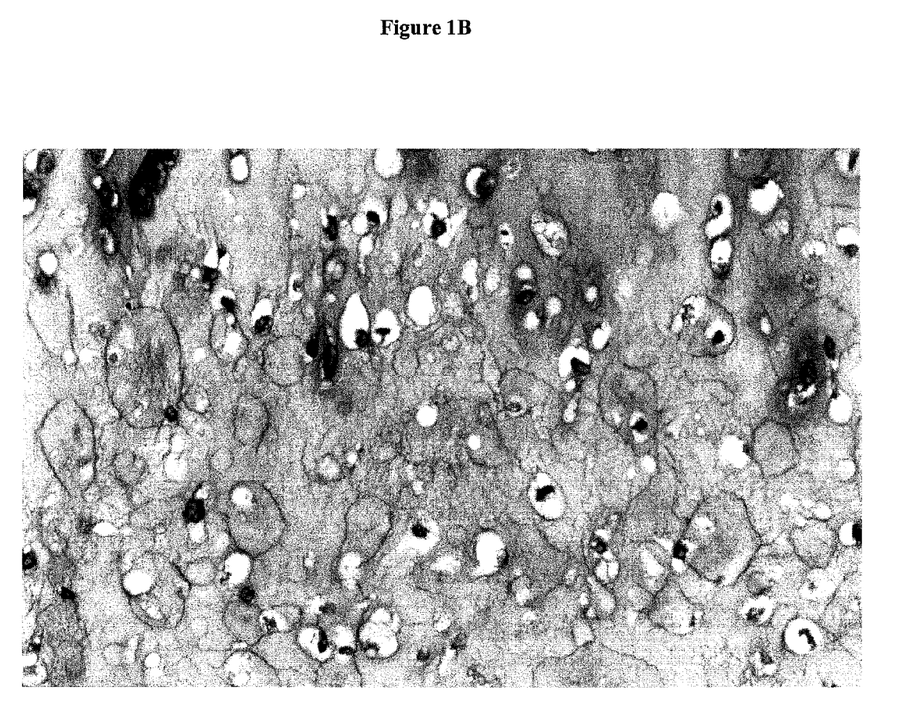
FIG. 1B is a photomicrograph of in vitro formed 8 week old nucleus pulposus tissue (toluidine blue, magnification×600).
Figure 2:
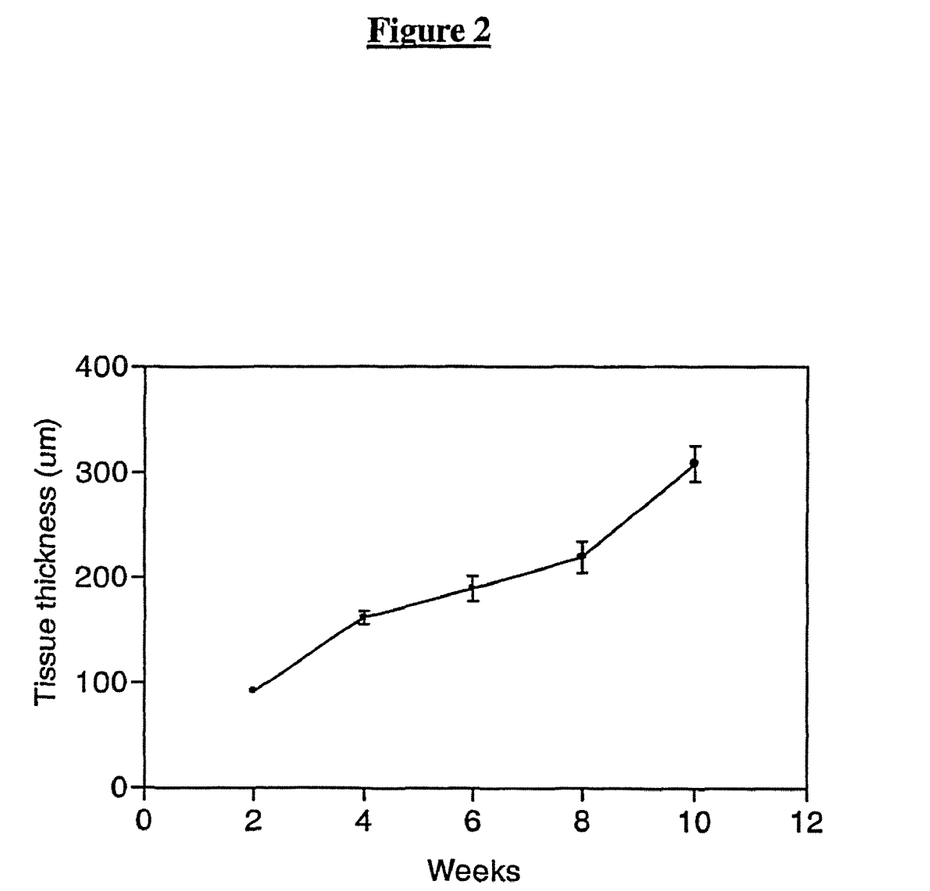
FIG. 2 shows the determination of culture tissue thickness over time. The cultures were harvested, paraffin-embedded and histological sections were used to measure the nucleus pulposus tissue thickness. The results are expressed as mean±SEM of three separate experiments and each time point was done in triplicate.

The nucleus pulposus cultures were examined histologically at 2, 4, 6, 8, and 10 weeks after initiation of the cultures to assess matrix accumulation and tissue organization. By 2 weeks in cultures, the nucleus pulposus cells accumulated extracellular matrix to form a continuous layer of tissue which contained sulfated proteoglycans as demonstrated by toluidine blue staining. Histologically, the extracellular matrix tissue appeared more abundant over time in culture (FIG. 1A). The cells were in lacunae similar to the in vivo nucleus pulposus tissue (FIG. 1B). The tissue thickness was measured in the histological sections, and it increased in thickness up to 10 weeks in culture. The nucleus pulposus tissue which had been dehydrated and paraffin embedded, attained a thickness of 308.8±29 μm (mean±SEM) at 10 wk. (FIG. 2).

Tissue Dry Weight

Figure 3:
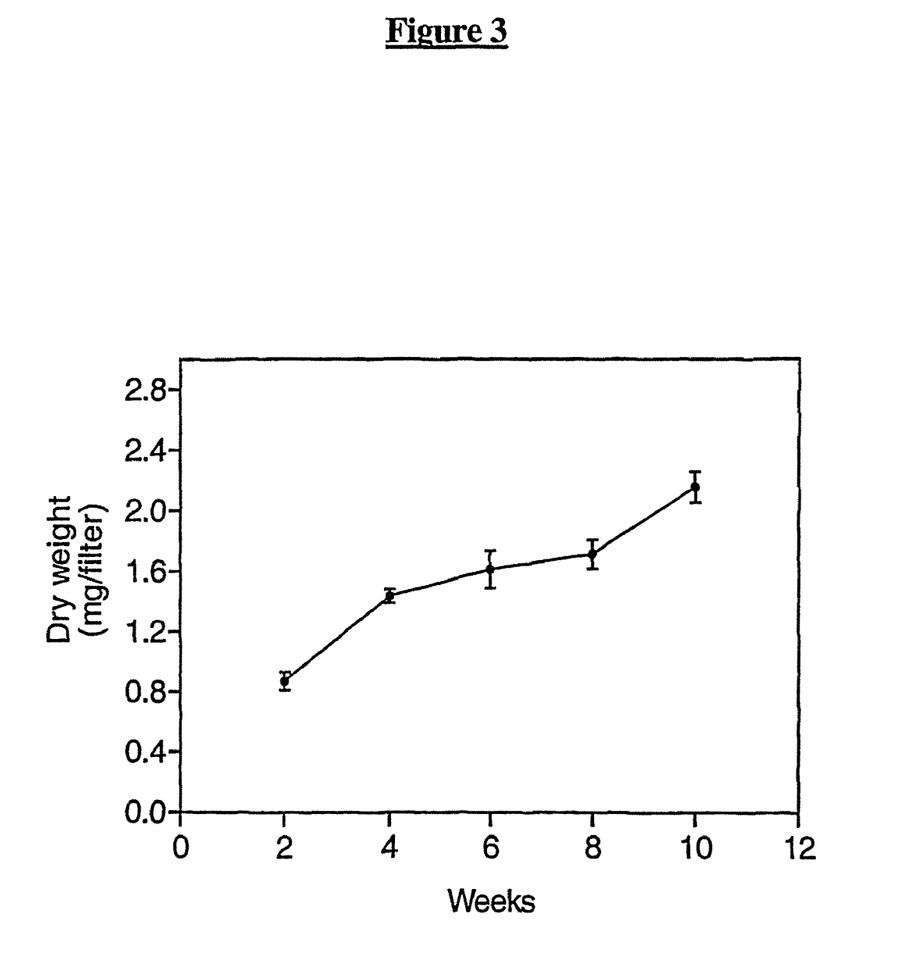
FIG. 3 shows the determination of culture tissue dry weight over time. The cultures were harvested, lyophilized and weighed. The results are expressed as mean±SEM of three separate experiments and each time point was done in triplicate.

The dry weight of the in vitro nucleus pulposus tissue increased over time up to 10 weeks. The dry weight of the tissue, which was 0.87±0.1 mg per culture (mean±SEM) at 2 weeks, weighed 2.16±0.2 mg per culture (mean±SEM) by 10 weeks (FIG. 3).

DNA Content of the Nucleus Pulposus Tissue

Figure 4:
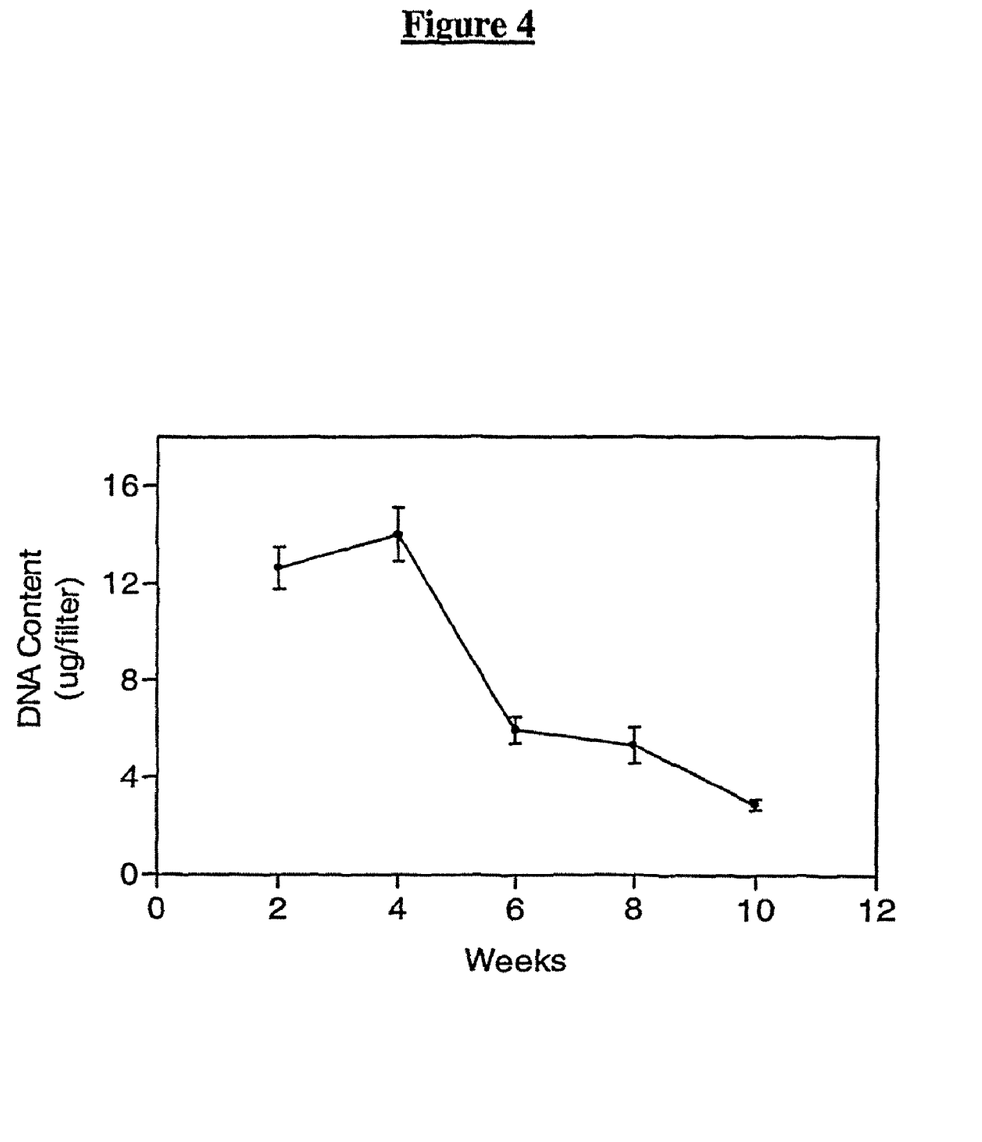
FIG. 4 shows the measurement of DNA content of the nucleus pulposus tissue in culture over time. The results are expressed as mean±SEM of three separate experiments and each time point was done in triplicate.

The DNA content of the nucleus pulposus tissue formed in culture was stable during the first 4 weeks in culture but then decreased over the following 6 weeks of culture. By 10 weeks the tissue cellularity had plateaued. (FIG. 4). The tissue formed in vitro at 10 weeks contained 1.25±0.02 μg DNA/mg dry weight (mean±SEM), whereas the in vivo nucleus pulposus contained 1.04±0.08 μg DNA/mg dry weight (mean±SEM). There was no significant difference between the in vitro formed tissue and the in vivo tissue.

Quantification of Proteoglycan and Collagen Content

Figure 5:
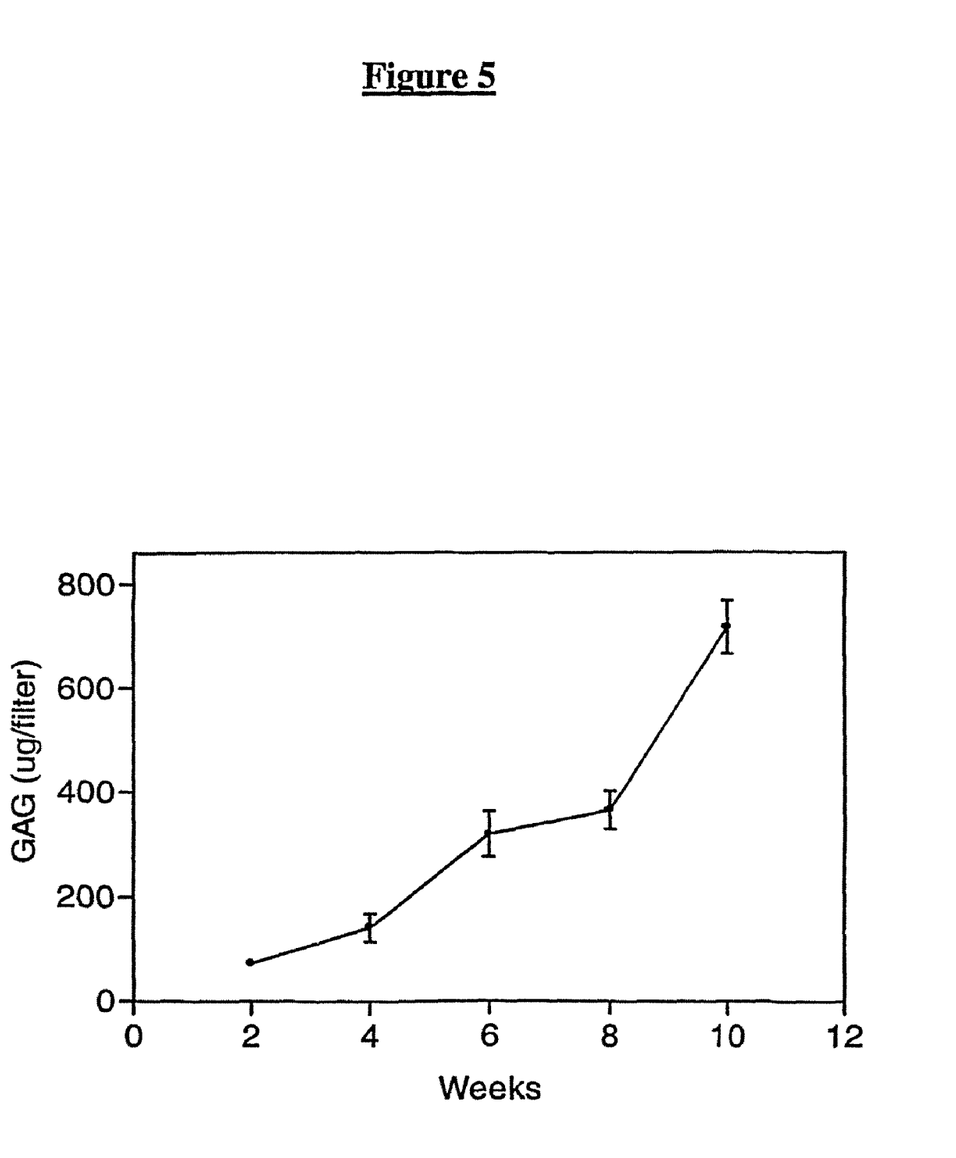
FIG. 5 shows the proteoglycan content of the nucleus pulposus tissue in culture over time which was determined by measuring glycosaminoglycan content. The results are expressed as mean±SEM of three separate experiments and each time point was done in triplicate.

Proteoglycans and collagen are the major macromolecules of the nucleus pulposus tissue. The proteoglycan and collagen contents in the extracellular matrix of the nucleus pulposus tissue in culture were quantified in order to examine matrix accumulation. The proteoglycan content, as determined by measuring glycosaminoglycan content, increased up to 10 weeks (FIG. 5). The tissue formed in vitro at 10 weeks contained 301.6±27.7 μg GAG/mg dry weight (mean±SEM), and 411±65 μg collagen/mg dry weight (mean±SEM), whereas the in vivo nucleus pulposus contained 320.6±21.2 μg GAG/mg dry weight (mean±SEM) and 399±44 μg collagen/mg dry weight (mean±SEM) (Table 1). There was no significant difference between the in vitro formed tissue and the in vivo tissue.

Analysis of the Proteoglycans and Collagens

Figure 6:
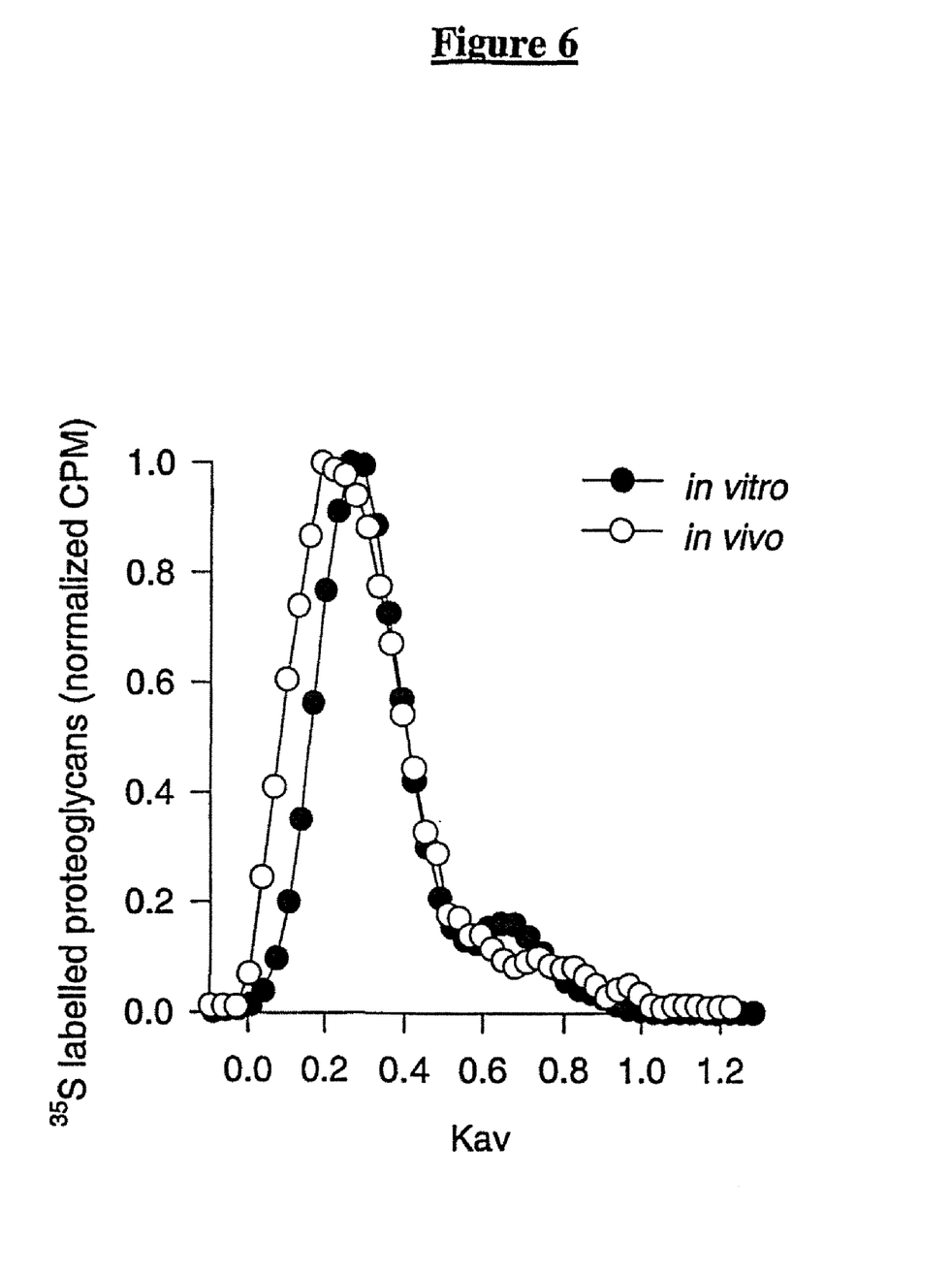
FIG. 6 shows proteoglycan elution profiles of newly synthesized proteoglycans extracted from 10 week old nucleus pulposus cultures (•-•) and of proteoglycans extracted from nucleus pulposus ex-vivo cultures (o-o). The size ($K_{av}$) of newly synthesized proteoglycan monomers was determined by gel chromatography (Sepharose CL-2B) under dissociative conditions. These are representative profiles from one experiment which was repeated three times.

As large proteoglycans and type II collagen are the main macromolecules present in the matrix of nucleus pulposus tissue, the proteoglycans and collagens present in the nucleus pulposus tissue formed in vitro were analyzed to determined whether the phenotype of these cells was retained under these culture conditions. To determine the size of the proteoglycans retained in the matrix, the [$^{35}$S]-sulphate labeled proteoglycans were guanidinium extracted from 8 week old culture. As shown in FIG. 6, analysis by column chromatography under dissociative conditions demonstrated that the proteoglycan monomers have a large hydrodynamic size ($K_{av}$=0.26±0.03, mean±SD), which was similar in size to those synthesized by cells in the ex vivo tissue cultures ($K_{av}$=0.22±0.02, mean±SD, p>0.05). Nucleus pulposus cells in vitro and in vivo were also synthesizing a smaller population of proteoglycan with a $K_{av}$ around 0.7.

Figures 7A, 7B:
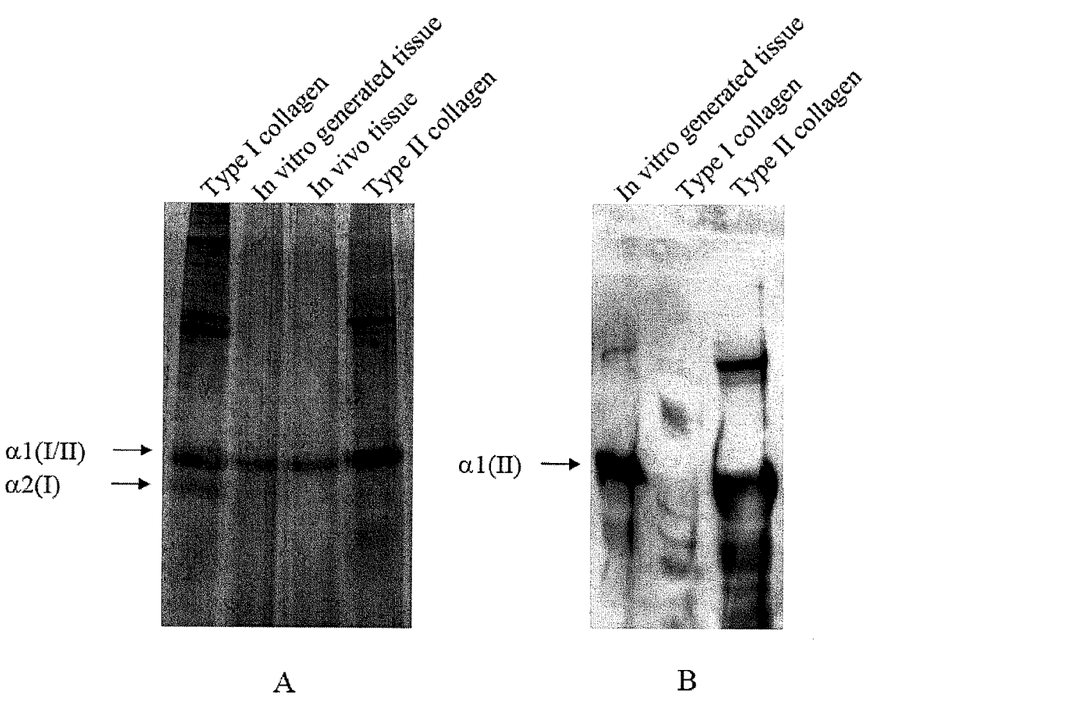
FIG. 7 shows the analysis of collagens in the nucleus pulposus tissue formed in vitro. (A) This is a representative polyacrylamide gel of pepsin-extracted collagens from nucleus pulposus tissue after 10 weeks in culture and stained with silver. The locations of the α1(II) is indicated by arrow (→). Western blot analysis of the pepsin extracts of the nucleus pulposus tissue formed in vitro using antibodies reactive with anti-type II (B). Type II collagen was detected in nucleus pulposus tissue after 10 wk in culture. Type I and type II collagen standards were run as controls.

Pepsin extracts of 10 week old tissue formed in vitro were analyzed by SDS-PAGE and autoradiography. A band similar in size to the α1(II) chain of type II collagen was seen. Western blot analysis of these extracts confirmed the presence of type II collagen (FIG. 7).

Discussion

A cell culture system is described herein in which nucleus pulposus cells isolated from sheep lumbar spines and grown on Millipore CM® filter inserts accumulate extracellular matrix and form a continuous layer of nucleus pulposus tissue. The nucleus pulposus cells in these cultures maintained their phenotype as they synthesized large sulfated PGs and type II collagen which are characteristic of nucleus pulposus cells. Cells isolated from rabbit nucleus pulposus also generated tissue in culture under similar conditions.

The composition of the in vitro formed tissue was similar to the ill vivo nucleus pulposus tissue. The cellularity and proteoglycan content at 10 weeks was comparable to the in vivo tissue. The predominate proteoglycan in the nucleus pulposus is aggrecan (Melrose 1994, Oegema 1979), and the cells in filter culture synthesized large proteoglycans in keeping with this type of proteoglycan. The size of proteoglycans synthesized by the nucleus pulposus cells in vitro was similar to that synthesized by the nucleus pulposus cells in ex-vivo culture as determined by column chromatography. As well a smaller amount of proteoglycans with a $K_{av}$ of approximately 0.7 were also detected. Proteoglycans of this size may represent degradation products or the presence of the small proteoglycans, such as decorin, fibromodulin, which have been shown to be present in the nucleus pulposus (Melrose 1994; Inkinen 1998; Jahnke 1988; Sztrolovics 1999; Gotz, 1997).

The cellularity of the in vitro tissue decreased between 4 and 10 weeks of culture and in doing so more closely approximates the cellularity of the in vivo tissue. The nucleus pulposus in vivo has been shown to become less cellular with age (Trout 1982; Buckwalter 1995). Other studies have shown that DNA content increases with time when nucleus pulposus cells were cultured in either monolayer or alginate gel. In these culture systems the cells do not synthesize sufficient matrix to form a continuous layer of tissue, so it is possible that the nucleus pulposus cells are in a different microenvironment than those present in the in vivo tissue (Chiba 1997, Sato 1999, Ichimura 1991).

This new culture system has several advantages over other culture systems in that the nucleus pulposus cells do not dedifferentiate, as indicated by the maintenance of their phenotype during the time period studied, and form a continuous layer of tissue which is amenable to histological and biochemical assessment. In addition the nucleus pulposus cells under these culture conditions maintain their phenotype. Other methods to culture nucleus pulposus cells have been described and include growing cells in monolayer (Ichimura 1991) or encapsulated within alginate (Chelberg 1995; Chiba 1997, Sato 1999 Maldonado 1992). However, these do not result in tissue formation and so do not mimic the organization of the nucleus pulposus tissue i.e. they do not accumulate sufficient extracellular matrix to form a continuous layer of tissue and so do not form a three dimensional structure. For example, nucleus pulposus cells grown in monolayer or suspension culture do not accumulate sufficient extracellular matrix to form a continuous layer of tissue (Ichimura 1991, Osada 1996). Nucleus pulposus cells grown in alginate or agarose beads remain spherical and accumulate mainly type H collagen and large proteoglycans but still do not form tissue (Chiba 1997, 1998, Maldonado 1992, Chelberg 1995). Furthermore, it has been shown that molecules of up to 200,000 molecular weight are able to diffuse out of alginate and this may influence what is retained within the matrix of these cultures (Kupchik 1983). Kusior L J et al (1999) has reported that nucleus pulposus cells embedded in biocompatible polymers, such as polyglycolic acid and calcium alginate, will form tissue. However, the cell seeded scaffolds had to be implanted in nude mice for tissue formation to occur. Although organ culture of the intervertebral disc has been used to study metabolism of the whole tissue it can not been maintained at a comparable metabolism level to the in vivo tissue. (Urban 1981, Thompson 1991). Recently an alternative approach was described by Chiba et al. (1998) in which an intact disc was surrounded with alginate, however this method did not entirely inhibit the matrix loss that occurs during the first few days of culture.

In conclusion, these studies demonstrate that the nucleus pulposus cells grown on filters generate tissue similar to the in vivo tissue for the features examined.

EXAMPLE 2

Formation of Disc Construct

The possible formation of a composite of nucleus pulposus tissue fused to cartilage which is anchored to the porous CPP was investigated. Articular chondrocytes were plated on the porous CPP discs and allowed to grow for 3 weeks. Simultaneously nucleus pulposus cells were grown on Millipore CM® filters as described above. At 3 weeks, a piece of nucleus pulposus tissue formed in vitro was punched out from the Millipore CM® filter and placed on the CPP-cartilagenous tissue construct that had been prepared. The tissue components were held together using fibrin glue and maintained in culture for 3 weeks. The composite was harvested and light microscopical examination of the processed constructs showed that substantial fusion of nucleus pulposus tissue with the underlying cartilagenous tissue occurred.

EXAMPLE 3

Generation of an Intervertebral Disc-CPP Biomaterial Construct

One half of an intervertebral disc fused to a cartilage endplate integrated with subchondral bone. To more closely mimic a natural disc, CPP will be generated with a central depression on its surface, the diameter of which will depend on the diameter of the CPP cylinder and with a depth of 0.5 mm. Articular chondrocytes can be isolated from sheep knee joint as described previously (Boyle et al, 1995) and plated in this depression. The cells will be grown under standard tissue culture conditions for 3 weeks during which time they will form cartilagenous tissue. Annulus fibrosus and nucleus pulposus cells will be isolated from sheep lumbar spine. The nucleus pulposus cells will be plated on filter inserts (Millicell CM®, Millipore Corp) and grown as described above for 4 wks (see Example 1). At 4 weeks the nucleus pulposus tissue formed in vitro has sufficient strength to be handled. The annulus fibrosus cells will be plated on top of the cartilagenous tissue which has formed on the CPP porous cylinder. This composite will be grown in culture for 4 weeks under the optimal loading conditions described herein. At 4 weeks a 2 mm diameter plug of annulus fibrosus tissue will be punched out from the centre and a plug of nucleus pulposus tissue (obtained from the nucleus pulposus tissue culture) will be placed in the resulting defect. In preliminary studies, no dead cells were seen at the edge of the punched out nucleus pulposus tissue suggesting that this manipulation does not damage the tissue. This composite consisting of annulus fibrosus, nucleus pulposus, cartilage endplate and CPP will then be grown in culture for an additional 4 to 6 wks under loading as defined above.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

TABLE 1

| Comparison of 10 week old in vitro generated nucleus pulposus tissue with in vivo nucleus pulposus tissue | | |
|---|---|---|
| | in vitro | in vivo |
| | (µg/mg dry weight) | |
| DNA | 1.25 ± 0.02 | 1.04 ± 0.08 |
| GAG | 301.6 ± 27.7 | 320.6 ± 21.2 |
| COLLAGEN | 411 ± 65 | 399 ± 44 |

The dry weight, and DNA, glycosaminoglycans (GAG) and collagen (hydroxyproline) contents were determined as described in Example 1. The analyses were performed on three different samples from each of three separate experiments. The data are expressed as mean±SEM of the three experiments.

REFERENCES

Simon S R, et al. In: Orthopedic Basic Science Ed. S R Simon, Am Academy of Orthopedic Surgeons, USA, 1994, 558-568

Bogduk N. The inter-body joints and the intervertebral discs. In: Bogduk N, Ed, Clinical Anatomy of the lumbar spine and sacrum. Churchill Livingstone, New York, 1997, pp: 13-31

Eyre D R. Biochemistry of the Intervertebral Disc. Int Rev Conn Tiss Res 8:227-291, 1979

Buckwalter J A. Aging and Degeneration of the Human Intervertebral Disc. Spine 20(11):1307-14, 1995

Chiba K, Andersson G B J. Masuda K., Momohara S. Williams J M, Thonar E J-M A. A New Culture System to Study the Metabolism of the Intervertebral Disc In Vitro Spine 23(17):1821-1828, 1998

Nerlich A, Boos N, Wiest I, Aebi M. Immunolocalization of major interstitial collagen types in human lumbar intervertebral discs of various ages. Virchows Arch 432:67-76, 1998

Inerot S, Axelsson I. Structure and Composition of Proteoglycans from Human Annulus Fibrosus. Conn Tiss Res 26:47-63, 1991

Roberts S, Caterson B, Evans H, Eisenstein, S M. Proteoglycan components of the intervertebral disc and cartilage endplate: an immunolocalization study of animal and human tissues. Histochem J 26:402-11, 1994

Antoniou J, Steffen T, Nelson F, Winterbottom N, Hollander A P, Poole R A, Aebi M. The Human Lumbar Intervertebral Disc. Evidence for Changes in the Biosynthesis and Denaturation of the Extracellular Matrix with Growth Maturation, Aging and Degeneration. J Clin Invest 98(4): 996-1103, 1996

Sztrolovics R, Alini M, Roughley P J, Mort, J S. Aggrecan degradation in human intervertebral disc and articular cartilage. Biochem J. 15:326(Pt. 1):235-41, 1997

Gotz W, Barnert S, Bertagnol, R, Miosge N, Kresse H, Herken, R. Immunohistochemical localization of the small proteoglycans decorin and biglycan in human intervertebral discs. Cell Tiss Res 289:185-190, 1997

Sztrolovics R, Alini M, Mort J S, Roughley P J. Age-related changes in fibromodulin and lumican in human intervertebral discs. Spine 24(17):1765-71, 1999

Bayliss M T, Johnstone B, O'Brien J P. Proteoglycan Synthesis in the Human Intervertebral Disc. Variation with Age, Region and Pathology. Spine 13(9): 972-981, 1988

Aguiar D J, Johnson S L Oegema Jr., T R. Notochordal Cells Interact with Nucleus Pulposus Cells: Regulation of Proteoglycan Synthesis. Exp Cell Res 246:129-137, 1999

Oegema T R. Biochemistry of the intervertebral disc. Clin Sports Med. 12:419-39, 1993

Aulisa L, Tamburrelli F, Lupparelli S, Tartarone M, Padua R. Immunohisto-chemical investigation on type III and VI collagen organization in human intervertebral discs in the neonatal period. Childs Nerv Syst 14(3):104-8, 1998

Rufai A, Benjamin M, Ralphs Jr. The development of fibrocartilage in the rat intervertebral disc. Anat Embryol (Berl) 192(1):53-62, 1995

Antoniou J, Goudsouzian N M, Heathfield T F, Winterbottom N, Steffen T, Poole A R, Aebi M, Alini M. The human lumbar endplate. Evidence of changes in biosynthesis and denaturation of the extracellular matrix with growth, maturation, aging, and degeneration. Spine. 21(10):1153-61, 1996

Thompson J P, Oegema T R Jr, Bradford D S. Stimulation of mature canine intervertebral disc by growth factors. Spine. 16:253-60, 1991

Handa T, Ishihara H, Oshima H, Osada R, Tsuji H, Obata K. Effects of Hydrostatic Pressure on Matrix Synthesis and Matrix Metalloproteinase. Production in the Human Lumbar Intervertebral Disc. Spine 22(10):1085-1092, 1997

Ishihara H, McNally D S, Urban J P G, Hall A C. Effects of hydrostatic pressure on matrix synthesis in different regions of the intervertebral disk. J Appl Physiol. 80:839-846, 1996

Miller J A A, Schmatz B S, Schultz A B. Lumbar Disc Degeneration: Correlation with Age, Sex and Spine Level in 600 Autopsy Specimens. Spine. 13(2):173-78, 1988

Ozali S, Muro T, Ito S, Mizushima M. Neovascularization of the outermost area of herniated lumbar intervertebral discs. J Orthop Sci. 4(4):286-92, 1999

Hadjipavlou A G, Simmons J W, Pope M H, Necessary J T, Goel V K. Pathomechanics and Clinical Relevance of Disc Degeneration and Annular Tear: a Point-of-View Review Am J Orthop 28:561-571, 1999

Kawaguchi Y, Osada R, Kanamori M, Ishihara H, Ohmori K, Matsui H, Kimura T. Association Between an Aggrecan Gene Polymorphism and Lumbar Disc Degeneration. Spine 24(23):2456-2460, 1999

Kraemer J. Natural Course and Prognosis of Intervertebral Disc Diseases. Spine 20(6): 635-639, 1994

Borenstein D G. Epidemiology, etiology, diagnostic evaluation, and treatment of low back pain. Curr. Opin. Rheumatol 11:151-157, 1999

Javedan S P, Dickman C A. Cause of adjacent-segment disease after spinal fusion. Lancet 354(9178):530-531, 1999

Leivseth G, Salvesen R, Hemminghytt S, Brinckmann P, Frobin W. Do human lumbar discs reconstitute after chemonucleolysis? A 7-year follow-up study. Spine 24(4): 342-7, 1999

Hou T-S, Tu K-Y, Xu Y-K, Li Z-B, Cai A-H, Wang H-C. Lumbar Intervertebral Disc Prosthesis. An Experimental Study. Chin Med J 104(5):381-3866, 1991

Enker P, Steffee A, Mcmillin C, Keppler L, Biscup R, Miller S. Artificial Disc Replacement. Preliminary Report with a 3-Year Minimum Follow-up. Spine 18(8): 1061-1070, 1993

Bao Q-B, McCullen G M, Higham P A, Dumbleton J H, Yuan H A. The artificial disc: theory, design and materials. Biomaterials 17:1157-1167, 1996

Kostiuk, J. P. Intervertebral Disc Replacement, Experimental Study. Clin. Orthop. Rel. Res. 337: 27-41, 1997

Zeegers W S, Bohnen L M L J, Laaper M, Verhaegen M J A. Artificial disc replacement with the modular type SB Charite III: 2-year results in 50 prospectively studied patients. Eur Spine J. 8:210-17, 1999

Choy D S. Percutaneous laser disc compression: 12 years experience with 752 procedure in 518 patients. J Clin Laser Med. Surg. 16(6):325-31, 1998

Nishida K, Kang J D, Suh J-K, Robbins P D, Evans C H, Gilbertson Lars G. Adenovirus-Mediated Gene Transfer to Nucleus Pulposus Cells Spine 23(22):2437-2443, 1998

Nishida K, Kang J D, Gilbertson L G, Moon S-H, Suh J-K, Vogt M T, Robbins P D, Evans C H. Modulation of the Biologic Activity of the Rabbit Intervertebral Disc by Gene Therapy: An In Vivo Study of Adenovirus-Mediated transfer of the Human transforming Growth Factor β1 Encoding Gene Spine 24(23) 2419-2425, 1999

Evans C H, Robbins P D. Genetically augmented tissue engineering of the musculoskeletal system. Clin Orthop 367 (Suppl):S410-8, 1999

Ichimura K, Tsuji H, Matsui H, Makiyama N. Cell Culture of the Intervertebral Disc of Rats: Factors Influencing Culture, Proteoglycan, Collagen and Deoxyribonucleic Acid Synthesis. J Spinal Disord 4(4):428-436, 1991

Maldonado B A, Oegema T R. Initial Characterization of the Metabolism of Intervertebral Disc Cells Encapsulated in Microspheres. J Orthop Res 10:677-690, 1992

Chelberg M, Banks G M, Geiger D F, Oegema T R. Identification of heterogeneous cell populations in normal human intervertebral disc. J Anat 186:43-53, 1995

Chiba K, Andersson G B J, Masuda K, Thonar E J-M A. Metabolism of the Extracellular Matrix Formed by Intervertebral Disc Cells Cultured in Alginate. Spine 22(24): 2885-2893, 1997

Kusior L J, Vacanti C A, Bayley J C, Bonassar L J. Tissue Engineering of Nucleus Pulposis in Nude Mice. Trans Orthop Society 45:807, 1999

Melrose J. Ghosh P. Taylor T K F: Proteoglycan heterogeneity in the normal adult ovine intervertebral disc. Matrix Biology 14: 61-75, 1994

Inkinen R I, et al. Relative increase of biglycan and decorin and altered chondroitin sulfate epitopes in the degenerating human intervertebral disc. J. Rheumatol 25:506-514, 1998

Jahnke M R, McDevitt C A: Proteoglycans of the human intervertebral disc: Electrophoretic heterogeneity of the aggregating proteoglycans of the nucleus pulposus. Biochem J 251: 347-356, 1988

Trout J J, et al: Ultrastructure of the human intervertebral disc: II. Cells of the nucleus pulposus. Anat Record 204: 307-314, 1982

Sato M et al: Phenotype stability and loss of heterogeneity of rabbit intervertebral disc cells in three-dimensional culture. Trans Orthop Res Soc 24: 1026, 1999.

Osada R et al: Autocrine/paracrine mechanism of insulin-like growth factor-1 secretion, and the effect of insulin-like growth factor-1 on proteoglycan synthesis in bovine intervertebral discs. J Orthop Res 14: 690-699, 1996

Kupchik H Z et al: A new method for the three-dimensional in vitro growth of human cancer cells. Exp Cell Res 147: 454-460, 1983

Urban J P G, Maroudas A: Swelling of the intervertebral disc in vitro. Connect Tissue Res 9:1-10, 1981

Oegema T R et al: Aggregated proteoglycan synthesis in organ cultures of human nucleus pulposus. J Biol Chem 254: 10579-10581, 1979

Boyle et al, Osteoarthritis and Cartilage 3, 117-125, 1995

I claim:

1. A process for producing an engineered biological material comprising a substrate having thereon a continuous layer of nucleus pulposus tissue, said process consisting of:
    isolating only nucleus pulposus cells from intervertebral disc;
    placing isolated nucleus pulposus cells on a surface of a substrate selected from the group consisting of bone, an engineered biomaterial, and porous tissue culture inserts, and;
    culturing the nucleus pulposus cells on the substrate in growth media under suitable conditions so that the nucleus pulposus cells maintain their phenotype, accumulate extracellular matrix, and form a continuous layer of nucleus pulposus tissue on the substrate, wherein the nucleus pulposus tissue synthesizes large proteoglycans and type II collagen, and has a three-dimensional organization.

2. A process for producing an engineered biological material comprising a substrate having thereon a continuous layer of nucleus pulposus tissue, said process consisting of:
    isolating only nucleus pulposus cells from intervertebral disc;
    placing isolated nucleus pulposus cells on a surface of a substrate selected from the group consisting of bone, an engineered biomaterial, and porous tissue culture inserts, and;
    culturing the nucleus pulposus cells on the substrate in growth media under suitable conditions so that the nucleus pulposus cells maintain their phenotype, accumulate extracellular matrix, and form a continuous layer of nucleus pulposus tissue on the substrate, wherein the nucleus pulposus tissue layer synthesizes large proteoglycans and type II collagen and has a three-dimensional organization; and
    wherein the continuous layer of nucleus pulposus tissue on the substrate has a thickness of between about 100 to 500 μm.

3. The process according to claim 1 wherein the substrate is an engineered bone substitute.

4. The process according to claim 3 wherein the engineered bone substitute is formed from sintered calcium polyphosphate.

5. A process for producing an engineered biological material comprising a substrate having thereon a continuous layer of nucleus pulposus tissue, said process consisting of:
    isolating only nucleus pulposus cells from intervertebral disc;
    placing isolated nucleus pulposus cells on a surface of a substrate selected from the group consisting of bone, an engineered biomaterial, and porous tissue culture inserts, and;
    culturing the nucleus pulposus cells on the substrate in growth media under suitable conditions so that the nucleus pulposus cells maintain their phenotype, accumulate extracellular matrix, and form a continuous layer of nucleus pulposus tissue on the substrate, the nucleus pulposus tissue layer synthesizing large proteoglycans and type II collagen in a three-dimensional organization; and
    applying torsion, compression or shear force to the cultured cells.

6. The process according to claim 1, wherein the nucleus pulposus cells are isolated by digesting nucleus pulposus tissue from intervertebral disc.

7. The process according to claim 2, wherein the nucleus pulposus cells are isolated by digesting nucleus pulposus tissue from intervertebral disc.

8. The process according to claim 5, wherein the nucleus pulposus cells are isolated by digesting nucleus pulposus tissue from intervertebral disc.

9. The process according to claim 1, wherein the substrate is not alginate.

10. The process according to claim 2, wherein the substrate is not alginate.

11. The process according to claim 5, wherein the substrate is not alginate.

* * * * *